United States Patent [19]

Boguslawski et al.

[11] Patent Number: 5,543,302

[45] Date of Patent: Aug. 6, 1996

[54] PROTEASES OF ALTERED STABILITY TO AUTOLYTIC DEGRADATION

[75] Inventors: George Boguslawski, South Bend; Josephine Grosch, Elkhart; John W. Shultz, Elkhart; Sethuraman Subramanian, Elkhart, all of Ind.

[73] Assignee: Solvay Enzymes, Inc., Elkhart, Ind.

[21] Appl. No.: 159,211

[22] Filed: Nov. 30, 1993

Related U.S. Application Data

[63] Continuation of Ser. No. 843,363, Mar. 19, 1992, abandoned, which is a continuation of Ser. No. 199,532, May 27, 1988, abandoned.

[51] Int. Cl.$^6$ .......................... C12P 21/00; C07K 13/00; C12N 9/00
[52] U.S. Cl. .................. 435/69.1; 435/68.1; 435/69.2; 435/70.1; 435/71.1; 435/71.2; 435/172.3; 435/188; 435/219; 435/220; 530/300; 530/324; 530/350
[58] Field of Search .................... 435/68.1, 69.1, 435/69.2, 70.1, 71.1, 71.2, 172.3, 188, 219, 220; 530/300, 324, 350

[56] References Cited

PUBLICATIONS

Cunningham et al. (1987) J. Cell. Biochem, Supp. 11C, p. 224.
Muller et al. (1975) Hoppe–Seyler's Z. Physiol. Chem., vol. 356, pp. 1173–1175.
T. Maniatis, E. F. Fritsch, & J. Sambrook, "Molecular Cloning: A Laboratory Manual," Cold Spring Harbor Laboratory, pp. 250–251 (1982).
S. Chang and S. N. Cohen, Mol. Gen. Genet., vol. 168, pp. 111–115.
Schroeder et al., J. Biol. Chem., vol. 243, No. 11, pp. 2943–2949 (1968);.
Smith et al., J. Biol. Chem., vol. 244, No. 17, pp. 4704–4712 (1969);.
L. Band, D. G. Yansura & D. J. Henner, Gene, vol. 26, pp. 313–315 (1983).
Arlaud et al., Biochimica et Biophysican Acta., vol. 616, pp. 116–129 (1980);.
Gagnon et al., Biochemical Journal, vol. 225, pp. 135–142 (1985).
Smith et al. J. Biol. Chem., vol. 243, No. 9, pp. 2184–2191 (1968).
Jacobs et al., Nucleic Acid Research, vol. 13, No. 24, pp. 8913–8926 (1985).
M. J. Zoller & M. Smith, DNA, vol. 3, No. 6, pp. 479–488 (1984).
Mezes et al., FEBS letters, vol. 161, No. 2, pp. 195–200 (Sept. 1983).
T. Maniatis, E. F. Fritsch, & J. Sambrook, "Molecular Cloning: A Laboratory Manual," Cold Spring Harbor Laboratory, pp. 382–386 (1982).
S. L. Beaucage & M. H. Caruther, Tetrahedron Letters, vol. 22, pp. 1859–1862 (1980).
Birnboim & Doly, Nucleic Acid Research, vol. 7, p. 1513 (1979).
Sanger et al., Proc. Natl. Acad. Sci., USA, vol. 74, pp. 5463–5467 (1977).

Primary Examiner—W. Gary Jones
Assistant Examiner—Ardin H. Marschel
Attorney, Agent, or Firm—Willian Brinks Hofer Gilson & Lione

[57] ABSTRACT

Proteases are susceptible to autolytic degradation. The method of the invention provides a method to identify susceptible autolysis sites which are cleaved to produce a few discrete fragments. Once identified, amino acid(s) at or in the vicinity of the cleavage site may be chemically modified or the DNA sequence capable of encoding the amino acid present at the site may be changed or deleted by site directed mutagenesis to produce an autolysis stable protease. The invention is particularly applicable to alkaline proteases which are produced in large quantities and used as detergent additives. Stable alkaline proteases could then be used in liquid detergent formulations.

7 Claims, 3 Drawing Sheets

PROTEASES OF ALTERED STABILITY TO AUTOLYTIC DEGRADATION

This is a continuation application of application Ser. No. 07/843,363 filed Mar. 19, 1992, now abandoned, which is a continuation of application Ser. No. 07/199,532 filed May 27, 1988, now abandoned.

FIELD OF THE INVENTION

The invention relates to proteases having altered stability to autolytic degradation, a method of identifying sites of cleavage by autolysis and a method of altering autolytic stability. The invention is particularly applicable to alkaline proteases which are produced in large quantities by fermentation for use as detergent additives.

BACKGROUND OF THE INVENTION

Proteases are known to be subject to degradation by autolysis since these enzymes contain the same chemical bonds which are cleaved by proteolytic activity. However, it was generally believed that such degradation was generalized, yielding many random small fragments.

EP application 0130756 suggests improving the properties of alkaline proteases by site directed mutagenesis, including oxidative stability, pH activity profiles, $K_m$, $k_{cat}$, $k_{cat}/K_m$ ratios and substrate specificity. However, no mention is made of altering the stability of such proteases to autolytic cleavage.

WO 87/04461 discloses a method of producing thermally stable and pH stable subtilisin analogs by replacing Asn-Gly sequences in subtilisins.

DESCRIPTION OF THE FIGURES

FIG. 1 shows the pattern of elution of autolytic fragments of APL fractionated on a Sephadex G75 superfine gel filtration column. The fraction number, F, is shown on the abscissa and the absorbance, A, is shown on the ordinate. The absorbance peaks are labeled I, II and III, corresponding to uncleaved protein having a molecular weight of approximately 28,000 Daltons (Da); a fragment having a molecular weight of approximately 16,000 Daltons; and a fragment having a molecular weight of approximately 8,000 Daltons, respectively.

FIGS. 2 and 2a show a diagram for the construction of an expression vector for an altered APL gene. Endonucleases are indicated as follows: HC is HincII, HD is HindIII, X is XmnI, Bg is BglI, BS is BspmII, S is SacII, E is EcoRV, C is ClaI, Bm is BamHI. The steps shown as Roman numerals correspond to: step I, digest M13mp19 with HincII and HindIII; step II, digest original APL clone with XmnI and HindIII and isolate fragments; step III, ligate DNA's of steps I and II to produce M13APL; step IV, digest M13APL with HindIII and BglI; step V, anneal JS96 and JS97, oligonucleotides shown in Table 3; step VI, ligate DNA's of steps IV and V to produce M13APL96; step VII, digest M13APL96 with BspmII and SacII; step VIII, anneal JS98 and JS99 oligonucleotide shown in Table 3; step IX, ligate DNA's of steps VII and VIII to produce M13APL98; step X, digest M13APL98 with EcoRV; step XI, digest pRW33 with ClaI and HindIII and blunt off fragments; step XII, ligate DNA's of steps X and XI to produce M13expAPL; step XIII, digest M13expAPL with BamHI; step XIV, digest pCPP-4 with BamHI; and step XV, ligate DNA's of steps XIII and XIV to produce pAPL-EXP, an expression vector.

SUMMARY OF THE INVENTION

The invention is based on the discovery that autolytic cleavage of a protease reproducibly yields discrete polypeptide fragments.

Cleavage sites can be identified by preparing an aqueous solution of a protease; rapidly inactivating the protease to prevent progressive degradation of peptide fragments produced by autolysis; separating the peptide fragments under conditions which prevent reactivation of the protease; and, identifying the N-terminal amino acids of the separated fragments.

Once an autolytic cleavage site has been identified, the autolytic stability of protease can be altered by modifying the amino acids at or in the vicinity of the autolytic cleavage site. A preferred method of modification involves cloning a gene or segment thereof comprising a DNA sequence capable of encoding the protease or segment thereof containing the autolytic cleavage site; changing the sequence capable of encoding the amino acid present at or in the vicinity of the cleavage site, thereby producing a mutated gene capable of encoding for an enzyme altered at or in the vicinity of the cleavage site; and expressing the altered protease.

The invention is particularly useful for serine proteases such as chymotrypsin, trypsin, and especially for alkaline proteases which are produced in large quantities by fermentation and of which a substantial portion could be lost if autolytic degradation occurred.

The alkaline proteases having increased stability to autolytic degradation can be used in liquid detergent compositions in which presently available alkaline proteases are unstable. Proteases, such as neutral proteases, can be produced with decreased autolytic stability for uses such as contact lens cleaners where it would be preferred for the enzyme to have a short life time.

DEFINITIONS

Alkaline proteases are serine proteases like the subtilisins with broad specificity for peptide bond hydrolysis. These enzymes are stable and active in the pH range 6 to 12. MILEZYME®, SAVINASE® and ESPERASE® are a few of the alkaline proteases sold commercially as detergent additives.

Altering autolytic stability is defined to include increasing or decreasing the autolytic stability over that seen in the original protease.

Modification is defined to include chemical modification as well as genetic manipulation to reduce the rate of autolytic degradation. Modification should occur at or in the vicinity of the amino acids which comprise the susceptible polypeptide bond of those amino acids. The phrase "in the vicinity of" is defined herein to mean within three amino acids upstream or downstream of those amino acids forming the susceptible bond.

APL is an alkaline protease produced by *Bacillus licheniformis* and sold by Miles Inc., Elkhart, Ind. 46515 as MILEZYME®. The complete amino acid sequence of APL has been published in J. Biol. Chem., Vol. 243, No. 9, 2184–2191, 1968. The protein sequence and standard numbering system used generally with alkaline proteases is shown in Table 1. The sequence numbering is referenced to the sequence of subtilisin Carlsberg as shown in J. Biol. Chem., Vol. 243, No. 9, pages 2184–2191 (1968). The APL gene is the gene encoding the alkaline protease from *B. licheniformis*.

SAVINASE® is an alkaline protease sold by Novo, Danbury, Winton, Conn., which has the N-terminal amino acid sequence shown below:

```
   1                  5                   10                  15
H₂N—Ala—Gln—Ser—Val—Pro—Trp—Gly—Ile—Ser—Arg—Val—Gln—Ala—Pro—Ala—Ala—
```

ESPERASE® is an alkaline protease sold by Novo, which has the N-terminal amino acid sequence shown below:

```
   1                  5                   10                  15
H₂N—Gly—Thr—Val—Pro—Trp—Gly—Ile—Ser—Phe—Ile—Asn—Thr—Gln—Gln—Ala—His—
```

TABLE 1

Location of self-digestion fragments in the sequence of subtilisin Carlsberg (APL)

```
NH₂—Ala—Gln—Thr—Val—Pro—Tyr—Gly—Ile—Pro—Leu—Ile—Lys—Ala—Asp—Lys—Val—Gln—Ala—Gln—Gly—Phe—Lys—Gly—Ala—Asn—
    1                                    10                                         20
    └─────────── Pool II ──────────────────→

Val—Lys—Val—Ala—Val—Leu—Asp—Thr—Gly—Ile—Gln—Ala—Ser—His—Pro—Asp—Leu—Asn—Val—Val—Gly—Gly—Ala—Ser—Phe—
                        30                                         40                                      50

Val—Ala—Gly—Glu—Ala—Tyr—Asn—Thr—Asp—Gly—Asn—Gly—His—Gly—Thr—His—Val—Ala—Gly—Thr—Val—Ala—Ala—Leu—
                55  57                          60                                  70

Asp—Asn—Thr—Thr—Gly—Val—Leu—Gly—Val—Ala—Pro—Ser—Val—Ser—Leu—Tyr—Ala—Val—Lys—Val—Leu—Asn—Ser—Ser—Gly—
                        80                                                                  99  100

Ser—Gly—*Ser—Tyr—*Ser—Gly—Ile—Val+Ser—Gly—Ile—Glu—Trp—Ala—Thr—Thr—Asn—Gly—Met—Asp—Val—Ile—Asn—Met—Ser—Leu—
    102  103 104 105                108  Pool II                                                120
         └─────── Pool II ───────────→
         └───────────────────→

Gly—Gly—Ala—Ser—Gly—Ser—Thr—Ala—Met—Lys—Gln—Ala—Val—Asp—Asn—Ala—Tyr—Ala—Arg—Gly—Val—Val—Val—Val—Ala—Ala—
        130                                             140                                         150

Ala—Gly—Asn—Ser—Gly—Asn—Ser—Gly—Ser—Thr—Asn—Thr—Ile—Gly—Tyr+Pro—Ala—Lys—Tyr—Asp—Ser—Val—Ile—Ala—Val—Gly—
                    160            163 164                         170
                                                           └──── Pool III ───→

Ala—Val—Asp—Ser—Asn—Ser—Asn—Arg—Ala—Ser—Phe—Ser—Ser—Val—Gly—Ala—Glu—Leu—Glu—Val—Met—Ala—Pro—Gly—Ala—Gly—
                                180                                         190                            200

Val—Tyr—Ser—Thr—Tyr—Pro—Thr—Asn—Thr—Tyr—Ala—Thr—Leu—Asn—Gly—Thr—Ser—Met—Ala—Ser—Pro—His—Val—Ala—Gly—Ala—
                        210                                             220                                 230

Ala—Ala—Leu—Ile—Leu—Ser—Lys—His—Pro—Asn—Leu—Ser—Ala—Ser—Gln—Val—Arg—Asn—Arg—Leu—Ser—Ser—Thr—Ala—Thr—Tyr—
                                240                                                 250

Leu—Gly—Ser—Ser—Phe—Tyr—Tyr—Gly—Lys—Gly—Leu—Ile—Asn—Val—Glu—Ala—Ala—Ala—Gln—COOH
        260                                             270              275
```

DETAILED DESCRIPTION OF THE INVENTION

1. Identification of the Problem

It has been recognized that proteases are, by definition, capable of cleaving peptide bonds, and that since such bonds are present in proteases themselves, proteases would be subject to autolytic cleavage. Such cleavage is often called self digestion. Previously it was generally assumed that such cleavage proceeded randomly or perhaps progressively through the protease molecule thereby producing small fragments. However, examination of protein composition in a fermentation mixture used to produce APL indicated that discrete fragments were produced and that such fragments were relatively large.

2. Method of Identifying Cleavage Sites

Autolysis apparently occurs when an aqueous solution of protease is prepared. After initial autolysis, it is speculated that the cleaved enzyme becomes susceptible to generalized autolytic cleavage which then results in the generalized degradation and production of small fragments. Therefore any uncleaved protease must be inactivated rapidly to prevent degradation of the fragments. It was found that it is possible to stop autolytic degradation in a protease solution and determine the amino acid site(s) cleaved. Rapid inactivation can be accomplished by adding trichloroacetic acid (TCA) to produce a final concentration of from 5 to 50% by weight, preferably about 10%. The peptide fragments are separated under conditions which prevent reactivation of the protease. One method comprises collecting the protease and peptide fragments precipitated by the TCA treatment by centrifugation, and resuspending the protein pellet collected by centrifugation in a solution of formic acid. The protein and polypeptide fragments obtained can be separated by fractionation on a molecular sieve column. However, other methods of separation, such as gel electrophoresis, high pressure liquid chromatography, starch gel electrophoresis, or paper chromatography, as are well known in the art, can also be used.

Although the method is generally applicable to proteases such as serine proteases, it will be illustrated specifically with respect to alkaline protease with examples of APL, ESPERASE and SAVINASE. General terminology for a cleavage site is shown below:

where the scissile peptide bond is shown with an asterisk, *. The amino acid residues of the substrate are numbered $P_1$, $P_2 \ldots P_n$ towards the amino terminus and $P_1'$, $P_2' \ldots P_n'$ towards the carboxy terminus from the susceptible cleavage bond. Cleavage sites for ESPERASE and SAVINASE are defined by sequences of autolytic fragments shown in Table 6 and 4 respectively.

Once the cleavage fragments are separated, the sequence of these peptides at their amino termini can be determined. The sequences of the APL fragments are then compared to that determined for the protein from *B. licheniformis*, since this sequence has been published, and the position of these segments in the enzyme were determined. It is found that the fragments observed for APL are generated by cleavage of the protein at sites between 102–103, 104–105 and between 163 and 164. These sites are marked with an asterisk (*) on TABLE 1 and the range of amino acids in the vicinity of the cleavage site, which are therefore candidates for modification, are shown with brackets [ ].

Since the protein sequences of SAVINASE and ESPERASE are not available, an alignment procedure could not be used as is used with APL. However, it has been observed that the sequences of many alkaline proteases from various Bacillus species are sufficiently similar so that it is possible to align the sequences. Therefore, fragment sequences obtained from SAVINASE and ESPERASE were compared to the published sequence of the alkaline protease from *B. licheniformis* using a computer program for homology search. The program used is present on the 1986 version of the IBI (International Biotechnologies, Inc., New Haven, Conn.). DNA/protein Sequence Analysis Systems software, (disk 2, program D Search for Homology with a Subsequence). The following parameters were used: the entire peptide sequence of APL was entered; no single residue was forced to be a perfect match, all matches greater than 50% were calculated. Such a comparison indicated that one region in APL had a high degree of identity to the sequenced segments of SAVINASE and ESPERASE and that this region started with residue number 193 of APL.

3. Producing A Protease of Altered Autolytic Stability

Once a principal site of autolytic cleavage has been identified, the amino acids comprising the susceptible polypeptide bond or those in the vicinity of a susceptible bond can be modified by chemical or genetic manipulation (e.g., site directed or cassette mutagenesis) to produce an enzyme of altered stability. Cleavage sites are indicated by a * in table 1 for APL and the range of amino acids considered for modification by brackets [ ]. Cleavage sites for ESPERASE and SAVINASE are identified by the sequence of fragments as shown in Tables 6 and 4 respectively. When large scale fermentation is used to produce the protease, increased stability to autolysis can improve the yield and, therefore, the efficiency of production.

Cloning of the Alkaline Protease Gene for Mutagenesis of the Autolytic Sites in the Protein It is advantageous to clone the gene encoding an enzyme in order to modify the product of the gene. Specifically, an enzyme displaying resistance to autolytic cleavage can be most effectively produced by:

1. Cloning of the gene or segment thereof capable of encoding the enzyme;
2. mutation of the gene to produce a variant of the gene whose predicted product would not contain the natural residues at or in the vicinity of the cleavage site;
3. expression of the enzyme either from its own transcription and translation signals or following the replacement of these signals with more advantageous DNA elements;
4. purification of the native and mutant enzyme followed by demonstration of the resistance of the mutant protein to autolytic cleavage.

It is expedient either to clone the entire gene encoding the enzyme or clone as complete a segment of the gene containing the susceptible polypeptide bond or the modification range as can be readily obtained.

Identification of the DNA segment to be cloned can be done by Southern hybridization of digested chromosomal DNA from the organism producing the desired enzyme to probe sequences designed to bind to the gene encoding the enzyme. Such probe sequences can be obtained from analysis of a published sequence of the gene as was done for the APL gene (Nucleic Acid Research, Vol. 13, No. 24, pp 8913–8926, 1985). However, when the sequence of the desired gene is not available, probe sequences can be obtained by the process of reverse translation of protein sequences obtained from the desired enzyme such as those determined for identification of the autolytic cleavage sites in the enzyme. One skilled in the art can analyze the many potential probe sequences that are generated in such a way to determine those most likely to identify only the desired gene in the presence of the other DNA sequences present within the bacterial chromosome.

The DNA fragment encoding the desired gene can then be enriched by the process of gel isolation and can subsequently be physically fused to an easily identified DNA segment known in the art as a vector by the process known as DNA ligation. The fragment-vector construct, known as a clone, can be introduced into a bacterial host by the process of transformation and the desired clone can be identified by hybridization of the DNA from the transformed bacteria to the DNA probe described above. The DNA sequence of the clone can then be obtained by techniques commonly used in the art in order to confirm that the proper DNA segment has been cloned and to identify restriction sites and obtain sequence information necessary for subsequent alteration of the gene encoding the protein. It is understood that other methods can be used to produce the desired clone such as techniques relying on the purification of the RNA transcription product of the gene or those which use immunochemical methods for the identification of desired clones. Those sufficiently skilled in the art would be familiar with these various techniques.

Mutagenesis of the Cloned Gene Segment

Mutagenesis of the cloned genes for the purpose of substitution of offending residues can be performed following subcloning of the gene into a phage vector known as M13. Site directed mutagenesis by the procedures described by M. J. Zoller and M. Smith, DNA, Vol. 3, No. 6, pp 479–488, 1984 can be performed to alter the regions of the gene encoding the offending residues. Selection of the residues used to replace the offending amino acids can be determined by computer modeling of the protein if the tertiary structure of the protein is known. However, in general such information is not known. In such cases it is best to replace the offending residues with amino acids which have different chemical properties since such replacements would have the best chance of causing major alterations in the property of the protein. Although the technique of site directed mutagenesis can be employed as described, other mutagenic protocols such as cassette mutagenesis and localized random mutagenesis can also be used. An alternative to this approach would be to alter the offending residues chemically so that such residue would be either insensitive or more susceptible to attack by autolysis.

Expression of the Wild Type and Altered Protease Genes

If the intact gene is cloned, this gene segment can be fused to a vector capable of propagation in a host organism. Upon cloning of the gene in a host species such as E. coli, expression of the cloned DNA segment may occur fortuitously. If expression of the isolated DNA segment is not observed, as measured by detection of the enzyme in cultures of the host carrying the recombinant plasmid, the gene can be transferred to another host, such as B. subtilis, where production of the enzyme would be more likely. If the enzyme is still not produced, the DNA elements responsible for transcription and translation initiation on the gene could be exchanged for those which operate in the desired host species.

If an incomplete segment of the gene is isolated, as judged by the DNA sequence of the cloned DNA, the data obtained can, in turn, be used to isolate the missing gene segment. The two segments encoding the gene can then be fused to produce an intact copy of the gene. Alternatively, the missing DNA sequence can be synthesized if either the actual DNA or protein sequence of the absent region is known. Transcription and translation initiation regions for expression of the protein in the host organism of choice can be added to the partial gene. Work would proceed as described earlier in this section.

If either the essential protein sequence of the enzyme or DNA sequence of the gene has been obtained, the entire gene can be produced synthetically and no DNA isolation from the natural host would be needed. In addition a wide variety of vectors allowing plasmid maintenance are available and many DNA segments which allow the transcription and translation of foreign genes are known. Once expression of the native enzyme is observed, the natural gene can be replaced with the mutated gene for expression of the altered protein.

Determination of the Autolytic Sensitivity of the Various Enzymatic Forms Expressed Crude enzyme preparations obtained from various host species contain components which may mask the effect of autolysis on the enzyme of interest. It is therefore essential to remove contaminants which could affect autolysis, such as peptides or media components, before an accurate measurement of the effect of autolysis on these enzymes can be made.

SOURCES AND ABBREVIATIONS

VIRUSES

1. M13mp18 and M13mp19—An E. coli phage available from New England Biolabs, 32 Tozer Road, Beverly, Mass., 01915.

2. M13APL—An E. coli phage deposited with the ATCC accession number 40438, carrying a segment of APL DNA useful herein.

BACTERIAL STRAINS

1. JM105—An E. coli strain available from United States Biochemical Corp. P.O. Box 22400, Cleveland, Ohio, 44122.

2. GX4926—deposited at USDA Northern Regional Research Laboratory, Peoria, Ill., accession number B-15811 and described in WO 86/01825.

CHEMICALS

1. X-Gal—5-Bromo-4-chloro-3-indolyl-β-D-galactoside available from United States Biochemical Corp.

2. IPTG—Isopropyl-β-D-thiogalactopyranoside available from United States Biochemical Corp.

3. SDS—Sodium dodecyl sulfate

4. BSA—Bovine serum albumin

All concentration percentages (%), unless otherwise specified, are weight/weight.

PLASMIDS 1. pRW33—A plasmid carrying the penPC gene (FEBS letters, vol. 161, No. 2, pgs. 195–200)

2. pCPP-4—A *B. subtilis—E. coli* shuttle vector ATCC No. 37277

The following specific examples of APL, SAVINASE and ESPERASE further illustrate the invention but are not to be construed as limiting. This invention can be applied to any enzyme which is cleaved at many sites by autolysis, especially serine proteases and alkaline proteases of commercial use.

Standard amino acid abbreviations are used in the tables. The numbering of amino acid sites is standard for alkaline proteases as relates to the sequence of APL shown in Table 1.

EXAMPLES

Example 1

Alkaline Protease from *B. licheniformis* (APL). Self-digestion of APL in a Buffer Solution The enzyme having alkaline protease activity and obtained from *B. licheniformis*, APL, was incubated in a buffer solution composed of 0.05M Tris-HCl, pH 8.0. By gel electrophoresis, the solution was found to contain a limited number of protein fragments of lower molecular mass than the intact molecule.

Separation

Figure 1:
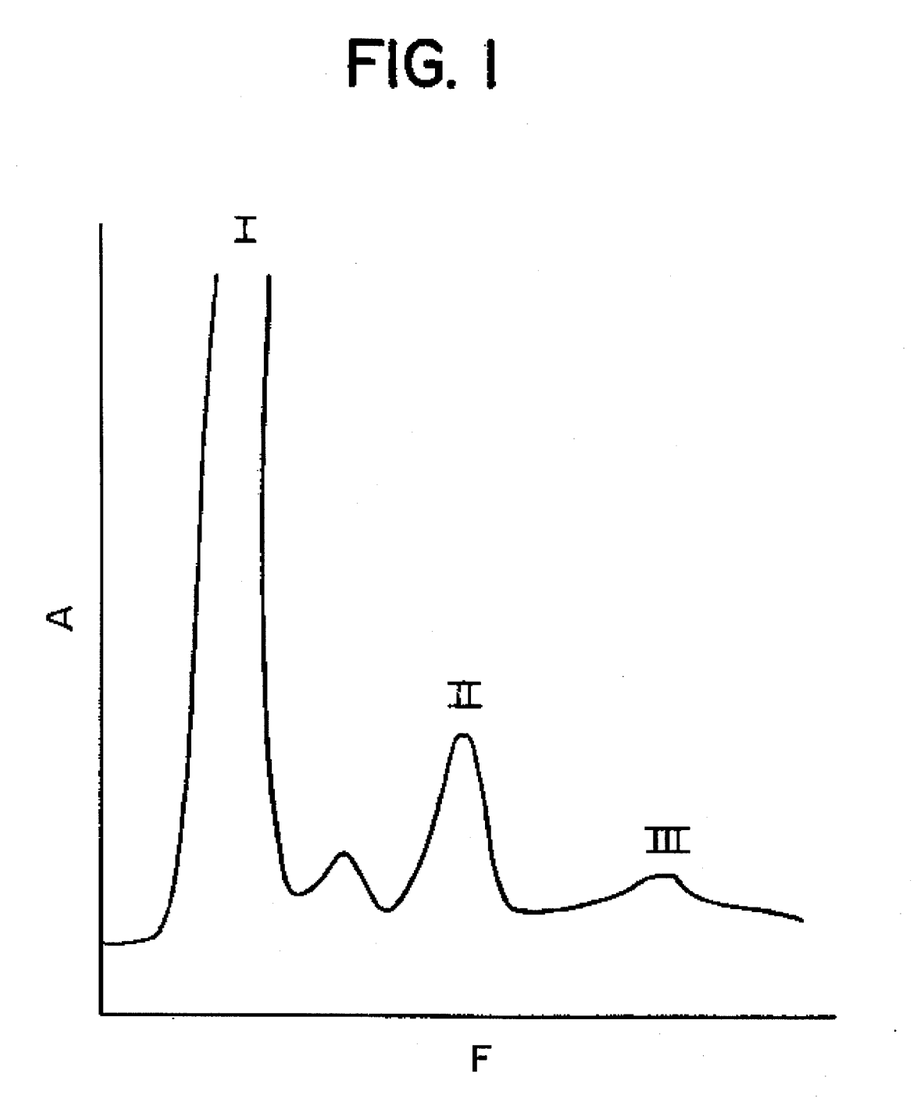

Fragments were separated by: (1) precipitation of the proteins by addition of TCA to 10%; (2) suspension of the protein in a small volume of 70% formic acid; and (3) fractionation of the protein using a Sephadex G75 or G50 Superfine column equilibrated with 9% formic acid. The elution of the peptide species was monitored at 280 nm with a UV detector, and fractions containing the various polypeptides were pooled and lyophilized (FIG. 1).

Identification

The pooled fragments were subjected to sequence analysis. Amino acid sequencing was performed using an Applied Biosystems Model 477A/120A sequence/analyzer system.

The amino acid residues released were identified manually by their elution from the HPLC system that is part of the sequencer. In some cases, as demonstrated in Table 2, more than one released residue was detected per sequenator cycle. In such cases, if the predominant residue was apparent, both residues are reported but the minor species is enclosed in parenthesis and is not included in the derived sequence. When it was impossible to confidently identify the predominantly released residue, both residues found were reported for the cycle and included in the derived sequence. In one case (Table 2, Pool II) several residues were released per cycle and all of these were reported. In this case, the derived sequences were obtained by a computer comparison of the released amino acids to the sequence of APL using the 1986 version of the IBI (International Biotechnologies, Inc., New Haven, Conn.) computer programs as described earlier. These derived sequences then identify the individual sequences that comprise the pool that generated the original data. The three sequences identified would have arose from degradation of segments of APL starting at amino acids 1, 103, and 105.

A similar computer analysis was performed on the Pool III sequence and the result of this analysis indicated that this sequence arose from degradation of the APL protein from residue 164. Thus fragments of APL naturally present in solutions of the protein were identified which had amino termini starting at residues 103, 105, and 164 of the intact protein. This indicates that autolytic degradation of the protein took place between residues 102 and 103, 104 and 105, and 163 and 164. This indicates that amino acids 102, 104 and 163 were principally recognized by the protease during the autolytic event, and as such would be the most likely residues to alter to effect this process. However, if an alteration could be made in the region of the sites which would prevent the polypeptide chain in this area of the protein from assuming a conformation that allows it to enter the active site of the protein, the autolytic event would be inhibited. Thus two types of changes could be designed, those in the region of an autolytic site that would affect the conformational stability of this region of the protein and others that take place at the site that would make it unpalatable to the protease. Alterations that would stabilize the conformation of the protein should not dramatically alter the basic structure of the protein, lest the activity of the enzyme be effected. Therefore such alterations should take place within several angstroms of the cleavage site, at or within three residues of the cleavage site.

TABLE 2

Sequence of APL Autolysis Fragments 8,000 Da fragment (Pool III)

| Residue | 1 | 2 | 3 | 4 | 5 | 6 | 7 | 8 | 9 | 10 | 11 | 12 |
|---|---|---|---|---|---|---|---|---|---|---|---|---|
| Amino Acid | — | Ile | Gly (Thr) (Ile) | Tyr (Val) | Pro (Phe) | Ala Gly (Ile) | Lys (Val) | Tyr Leu | Pro Ile | Ser Tyr | Val | Ile |
| Derived sequence | — | Ile | Gly | Tyr | Pro Gly | Ala | Lys | Tyr Leu | Pro Ile | Ser Tyr | Val | Ile |

16,000 Da fragments (Pool II)

| Residue | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Amino acid | Ala Gly Ser Asn Asp | Gln Gly Tyr Ile | Ser Thr Val Ile | Val Gly | Pro Ile | Gly Val Tyr Ala Ile | Gly Ile Met Ser | Ile Glu | Ala Pro | Ala Leu Glu Thr Ser | Ile Thr | Ala Asn Lys | Ala Asn | Met Asp | Met Ile Lys |

TABLE 2-continued

Sequence of APL Autolysis Fragments

| | | | | | | | | | | Met | | | | | |
|---|---|---|---|---|---|---|---|---|---|---|---|---|---|---|---|
| Derived | 1 | Ala | Gln | Thr | Val | Pro | Tyr | Gly | Ile | Pro | Leu | Ile | Lys | Ala | Asp | Lys |
| sequences | 2 | Ser | Tyr | Ser | Gly | Ile | Val | Ser | Gly | Ile | Glu | Trp | Ala | Thr | Thr | Asp |
| | 3 | Ser | Gly | Ile | Val | Ser | Gly | Ile | Glu | Trp | Ala | Thr | Thr | Asp | Gly | Met |

Cloning of a Portion of the Alkaline Protease Gene from *B. licheniformis*

A segment of the gene encoding the alkaline protease from *B. licheniformis* was cloned in order to modify the gene product to produce a more autolysis stable form. A DNA fragment carrying a segment of the gene was identified by Southern hybridization of the chromosomal DNA from *B. licheniformis* to a probe homologous to a selected region of APL (shown specifically later). Chromosomal DNA (10 µg) was digested with various restriction endonucleases, and the resulting DNA fragments were fractionated by electrophoresis using a 0.8% agarose gel and TBE buffer (10.8 g Tris, 5.5 g boric acid, 4 mL of 0.04M EDTA pH 8.0, per liter) following addition of 10× TBE sample buffer (formulation consisting of 0.06 g xylene cyanol, 0.06 g bromophenolblue in 10 mL of 50% glycerol). A sample of phage lambda DNA digested with restriction endonuclease HindIII was included on the gel to serve as a size standard. The DNA was electrophoresed overnight at low voltage (40 V) on a large agarose gel (6.5×6.0 inches). At this voltage, the bromophenolblue dye had migrated approximately 5 inches through the gel. The gel was stained by soaking in ethidium bromide (0.01 mg/mL) and photographed using short wave UV light. The separated DNA fragments were transferred to a nitrocellulose membrane by the method described in "Molecular Cloning: a Laboratory Manual", T. Maniatis, E. F. Fritsch, and J. Sambrook, 1982, Cold Spring Harbor Laboratory, pgs 382–386. The nitrocellulose filters were then prehybridized at 65° C. for three hours in 20 mL of 0.25% non-fat instant dry milk in 2× Saline Sodium Citrate (SSC). 20× SSC is made by dissolving 175.3 g of NaCl and 88.2 g of sodium citrate in 800 mL of water. The pH of the solution is adjusted to 7.0 and the solution is diluted to the desired strength before use without subsequent pH adjustment (unless specified). Following prehybridization, a $^{32}$P labeled probe described below was added to a final concentration of 2.5×10$^6$ cpm/mL, and the hybridization mixture was incubated overnight at room temperature on a rotary shaker. The membrane was washed three times in 20 mL of 2× SSC, 0.1% SDS at 50° C. for 10 minutes, dried in air and placed on an X-ray film. After several days, the exposed film was developed and the gel was shown to have only one hybridizing band in each lane of the fractionated, restricted DNA. The result confirmed that, at the proper stringency, only one DNA segment in *B. licheniformis* hybridized to the probe sequence used. The mobility of the hybridizing bands were then compared to the fragments from the standard and the molecular weights of the hybridizing fragments were estimated. It was found that the DNA fragment which carries the hybridizing region of the APL gene following restriction of the DNA with endonuclease HindIII was approximately 2.1 kb. The fragment was cloned to obtain a copy of APL gene.

The probes used to identify the APL gene were synthesized by using the phosphoramidite chemistry (Beaucage, S. L., Caruther, M. H. (1980) Tetrahedron Letters, Vol. 22, pp 1859–1862 on the Applied Bio-systems DNA Synthesizer, Model 380A, Foster City, Calif.) The synthesized oligonucleotides were purified by preparative polyacrylamide gel electrophoresis. The sequences of the probes used were:

5'AACGGAACGTCAATGGCTTCTCCTCACGTTGCCGGAGC and

5'CTTAGAAAGAATCAAAGCTGCTGCTCCGGCAACGTG

These probes were labeled with radioactively labeled deoxynucleotides as is well known in the art.

The cloning of the 2.1 kb fragment which carried a segment of the APL gene was initiated by digestion of chromosomal DNA (150 µg) from the *B. licheniformis* strain tested above with endonuclease HindIII (450 U) in a buffer composed of 100 mM NaCl, 50 mM Tris-HCL pH 7.5, 10 mM MgCl$_2$, and 1 mM dithiothreitol, in a volume of approximately 450 µL. The reaction mixture was incubated for several hours at 37° C. and then loaded onto a preparative 0.8% agarose gel. Lambda DNA digested with this endonuclease was again included on the gel as a size standard. The gel was run overnight at 40 V, and the DNA bands were stained with ethidium bromide as described above. The DNA was visualized under short wave UV light, and a slit was made through the gel in the lanes containing the digested chromosomal DNA across from the 2.0 kb DNA fragment present in the standard. The gel was returned to the electrophoresis chamber and a strip of DEAE cellulose was inserted into the slit in the gel. Current was applied to the gel until the 2.2 kb DNA fragment of the standard migrated to the position of the slit. The DEAE strip, now containing the DNA fragments ranging in size between 2.0 and 2.2 kb was removed from the gel and placed in a 1.5 mL Eppendorf tube. One milliliter of TE buffer (10 mM Tris-HCl, pH 7.5, 1 mM EDTA) was added to the tube and the contents of the tube were mixed by vortexing until the paper was pulverized. The microfuge tube was spun 5 minutes and the supernatant was discarded. The pellet was suspended in 1.0 mL of TE, spun 5 minutes in a microfuge and the supernatant was again discarded. The pellet was resuspended in 450 µL of 1.5M NaCl containing 40 mM arginine free base and the tube was shaken well for 10 minutes. The tube was centrifuged in a microfuge for five minutes and the supernatant, containing eluted DNA fragments, was placed in a fresh 1.5 mL Eppendorf centrifuge tube. A solution (900 µL) of 95% ethanol was added to the tube, the mixture was chilled at −70° C. for 15 minutes and spun in a microfuge as described above. The supernatant was discarded, the pellet was rinsed once in 70% ethanol and respun as above. The pellet was dried under vacuum and the DNA was resuspended in 20 µL of water.

Approximately 200 ng of M13mp19 was digested with endonuclease HindIII under the conditions described above except the final reaction volume was 50 µL. The digested DNA reaction mixture, to which 50 µL of water was added, was extracted with 100 µL of chloroform-phenol, and the aqueous layer was transferred to a 1.5 mL Eppendorf tube. A solution of 95% ethanol (900 µL) was added to the tube and the tube was chilled at −70° C. for 15 minutes. The tube was centrifuged in a microfuge 5 minutes, the supernatant was discarded and the DNA pellet was dried under vacuum. The following solutions were added to the DNA: 1 µL of 10× ligase buffer (0.5M Tris-HCl (pH 7.5), 0.1M MgCl$_2$, 0.1M dithiothreitol, 10 mM spermidine, 10 mM dATP, and 1 mg/mL BSA), 2 µL of the isolated fragments, 6 µL of water and 1 µL of T4 DNA ligase. The reaction mix was incubated for 1 hour at room temperature and the ligation reaction was used to transfect competent E. coli JM105 (competent cells produced by the procedure described in Maniatis et al, cited previously, pgs. 250–251, steps 1–5). Ten separate incubations, each using 1 µL of the ligation mixture, were performed each using one tube of competent cells. The competent cells and the ligated DNA were incubated 1 hour at 4° C. and the cells were then placed in a 42° C. water bath for 2 minutes. One milliliter of L-broth was added to each transfection and the mixture was then divided into six aliquots into sterile tubes. One drop of an overnight culture of JM105 was added to each tube. Three milliliters of top agar was then placed into each tube and the contents were gently mixed and plated onto L-agar plates spread with 100 µL each of 10 mg/mL X-Gal in dimethylformamide, and 100 mM IPTG. (Note that it is important to let these spread solutions dry before using the plates). The plates, incubated at 37° C. overnight, were found to contain blue plaques and clear plaques. The blue plaques indicated regions where cells carrying the M13mp19 vector devoid of insert DNA had grown. Clear plaques indicated regions where cells carrying the M13mp19 vector containing a DNA insert had grown. In all, three series of ligations and transfections were performed in order to obtain a library of approximately 600 clones containing insert DNA. When few clear plaque were present on a transformant plate, the clear plaques were individually picked and placed in a sterile test tube along with 15 µL of an overnight culture of JM105 and 1.5 mL of L-broth. The tubes were incubated for six hours at 37° C. and 200 rpm, ant the contents of the tubes were transferred to a 1.5 mL Eppendorf tubes and spun. After centrifugation, one microliter of each supernatant was spotted on a nitrocellulose filter. The rest of the supernatants were discarded and the cell pellets were frozen. The filter was air dried and baked at 80° C. for 30 minutes, and then hybridized as described for Southern blots of chromosomal DNA.

When the plates displayed many clear plaques, the plaques were lifted onto nitrocellulose. The discs were baked at 80° C. for 60 minutes under vacuum to immobilize the DNA. The hybridization with synthetic probes was then carried out as described for nitrocellulose blots of agarose gels. Two plaques were shown to hybridize strongly to the labeled probe, one plaque originating from the spotted cell supernatants, and the other from a plaque directly lifted from a plate. The plaque present on the plate was picked as an agar plug and propagated as described above for those picked from plates containing few clones. The cell pellet from both of these clone propagations were used to produce double stranded phage DNA by a protocol slightly modified from that of Birnboim and Doly, (Nucleic Acid Research, Vol. 7, p1513, 1979), and 1 µL samples of these DNAs were used to transfect fresh, competent JM105. Both of these transfections produced many clear plaques which displayed strong hybridization upon plaque lifting and reprobing as described above. Three strongly hybridizing plaques from each of the resulting progeny phage were picked and propagated in liquid by placing an agar plug containing the plaque in 1.5 mL of medium with 15 µL of JM105 from an overnight culture, and incubating the resulting mixture at 37° C. and 200 rpm for six hours. The supernatants from these cultures were saved and used for the preparation of template DNA. The DNA was sequenced by the techniques of Sanger et al, Proc. Natl. Acad. Sci., USA, Vol. 74, pp5463–5467, 1977. However, internal DNA primer segments, made to match the published sequence of the APL gene, were used in addition to the universal primer in order to obtain the sequence of the entire APL coding region present in this phage more rapidly. The derived sequence was shown to contain an open reading frame which, when translated, exactly matched the published protein sequence of APL from amino acid 55 of the mature protein to the carboxy-terminus of the protein.

The cloned region of the APL gene contains the residues shown to be sensitive to autolytic chain cleavage, and as such can be used for modification of the gene at this location to produce a protein which would be resistant to such cleavage.

The data reported above verify that the segment of the APL gene encoding the mature protein sequence from the amino acid 55 through the carboxy terminus of the protein had been cloned.

Subcloning of the APL Gene and Site Directed Mutagenesis of the Coding Region of the Gene The coding region of APL is flanked by HindIII and XmnI sites. These sites were used to subclone the desired DNA fragment into M13mp19 for the purpose of site directed mutagenesis, as described below.

Cell pellets obtained when the template phage DNA were prepared were used to produce double stranded DNA as described above. Approximately 200 ng of this DNA were digested with HindIII and XmnI and the resulting DNA fragments were fractionated on a 0.8% agarose gel. The fragment of approximately 750 base pairs was gel isolated as described earlier for chromosomal DNA. The isolated DNA fragment was mixed with approximately 200 ng of M13mp19 digested with HindIII and HincII. The DNAs were ligated and used to transfect competent JM105 as described above and several of the resulting clear plaques were used to obtain double stranded DNA as before. Restriction digestion and subsequent DNA sequence analysis performed as before confirmed that these clones contained the desired DNA segment necessary for site directed mutagenesis for modification of the gene in order to replace the offending residues in the encoded product. Template DNA was prepared from these clones as was done for sequencing of the original clone of the gene, and this DNA could be used to perform site directed mutagenesis.

Mutagenesis can then be performed as described in M. J. Zoller and M. Smith, DNA, Vol. 3, pp 479–488, No. 6, 1984. A mutagenic primer containing random base sequences at the autolytic cleavage sites can be used and the resulting mutant phage can be sequenced to identify the exact alterations that have been inserted into the gene. Those mutants having new sequences which change the chemical nature of the residues at the autolytic site are saved for later expression.

Expression of the Modified and Wild-Type APL Genes

Before the segment of the alkaline protease gene encoding APL can be used to express the full length mature protein, the DNA encoding the remaining amino acids comprising this segment of the protein must be added to the clone. This can be done by addition of synthetic DNA segments to the M13 subclone of APL described earlier referred to herein as M13 APL, deposited as lyophilized sterile bacteriophage with the ATCC, accession number 40438. It is convenient at this point to provide the desired clone with restriction endonuclease sites to make later additions easier.

In order to obtain DNA of the M13 APL clone for addition of the oligonucleotide segments, the M13 APL clone was retransformed into competent JM105 as described above and one of the resulting plaques was propagated in a 25 mL liquid culture as described above. From the cells obtained from this culture, double strand phage DNA was isolated by scaling up the procedure described above and the DNA was dissolved in 1 mL of water. A 50 µL portion of this DNA was digested with BglI and HindIII in a 500 µL total reaction volume. The digested DNA was extracted with 500 µL of phenol: chloroform (1:1), and the aqueous layer was mixed with 50 µL of 3M sodium acetate, pH 5, and 1.5 mL of 95% ethanol. The solution was chilled at −20° C. for 30 minutes and centrifuged in a microfuge at 13,000 rpm for 30 minutes. The supernatant was removed by decantation and the pellet, which contained the DNA, was dried under vacuum. The DNA was then dissolved in 300 µL of distilled water.

for further study and digested with EcoRV, and the resulting DNA fragments were analyzed as described above. All of these preparations were shown to linearize with this enzyme, which confirmed that these clones were correct. The new construction was given the name M13APL96, and these plasmid preparations were used for construction of the next vector.

The second pair (JS98 and JS99) of oligonucleotides could then be added to the M13APL96 clone as described above except that the phage DNA would be digested with SacII and BspMII. The result of this construction could then be identified as M13APL98. However, this clone would be unable to express the desired protein as it contains neither the proper DNA signals needed for transcription, translation and secretion of the APL, nor those needed for replication in our host of choice for expression of the gene, *B. subtilis*. The gene can be provided with the proper DNA sequences needed for expression by fusion of the APL gene segment on the phage to sequences known to provide such signals in *B. subtilis*, such as those arising from the subtilisin gene or penPC (FEBS Letters, Vol. 161, No. 2., pp 195–200, 1983) both of which encode proteins that are secreted. As will later become apparent, it is helpful to have the final product of

TABLE 3

JS 96:
5'-AGC CGG ATC CGA TAT CCG CGG CGC AAA TTT CCG GAC
TTG AAC GTA GTC GGC GGA GCA AGC TTT GTG CTG GGC GA-3'

JS 97:
5'-AGC TTC GCC AGC CAC AAA GCT TGC TCC GCC GAC TAC
GTT CAA GTC CGG AAA TTT GCG CCG CGG ATA TCG GAT CCG
GCT GAA-3'

JS 98:
5'-GGC GCA AAC CGT TCC TTA CGG CAT TCC TCT CAT TAA
AGC GGA CAA AGT GCA GGC TCA AGG CTT TAA GGG AGC GAA
TGT AAA AGT AGC CGT CCT GGA TAC AGG AAT CCA AGC TTC
TCA T-3'

JS 99:
5'-CCG GAT GAG AAG CTT GGA TTC CTG TAT CCA GGA CGG
CTA CTT TTA CAT TCG CTC CCT TAA AGC CTT GAG CCT GCA
CTT TGT CCG CTT TAA TGA GAG GAA TGC CGT AAG GAA CGG
TTT GCG CCG C-3'

Figure 2:
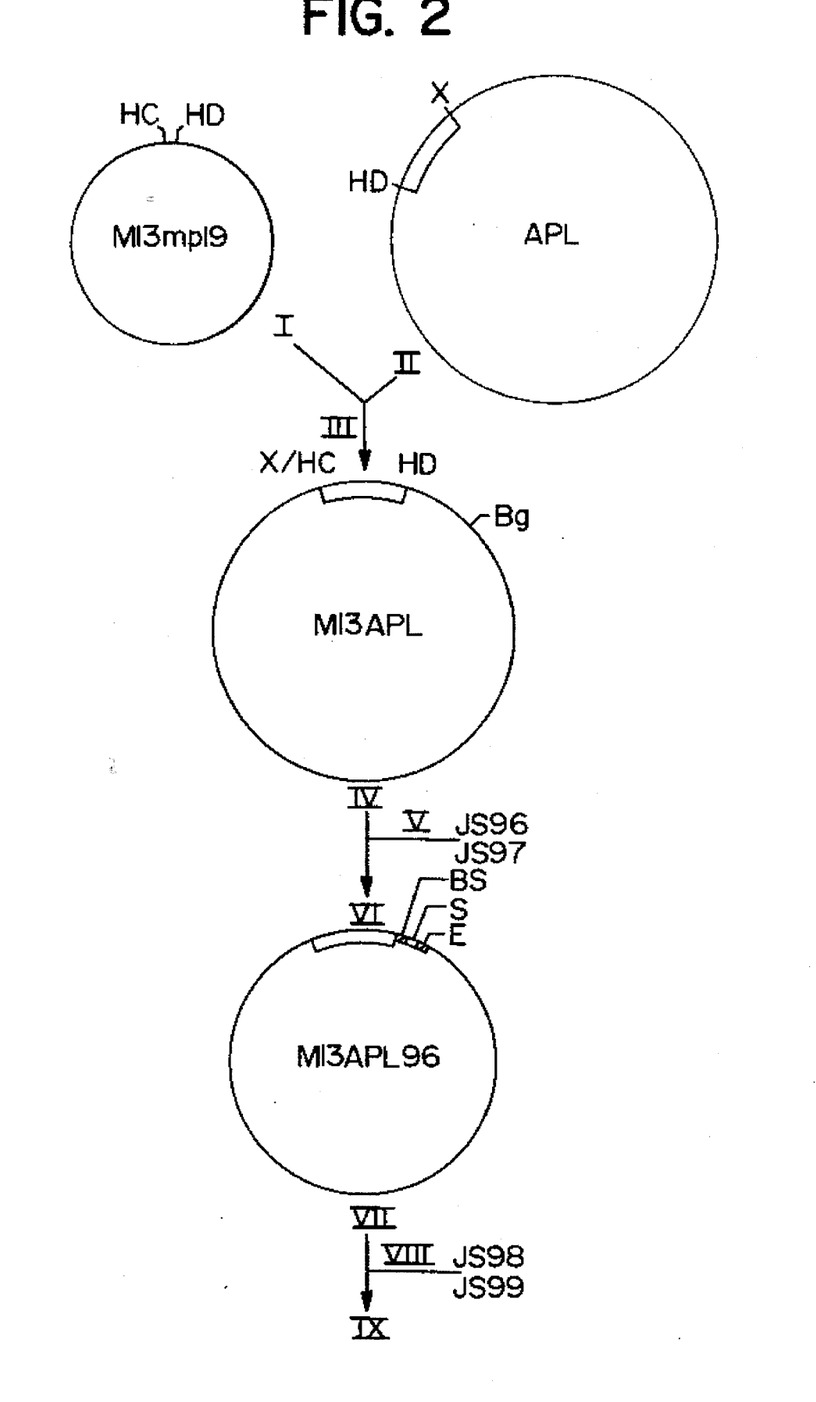
Figure 2A:
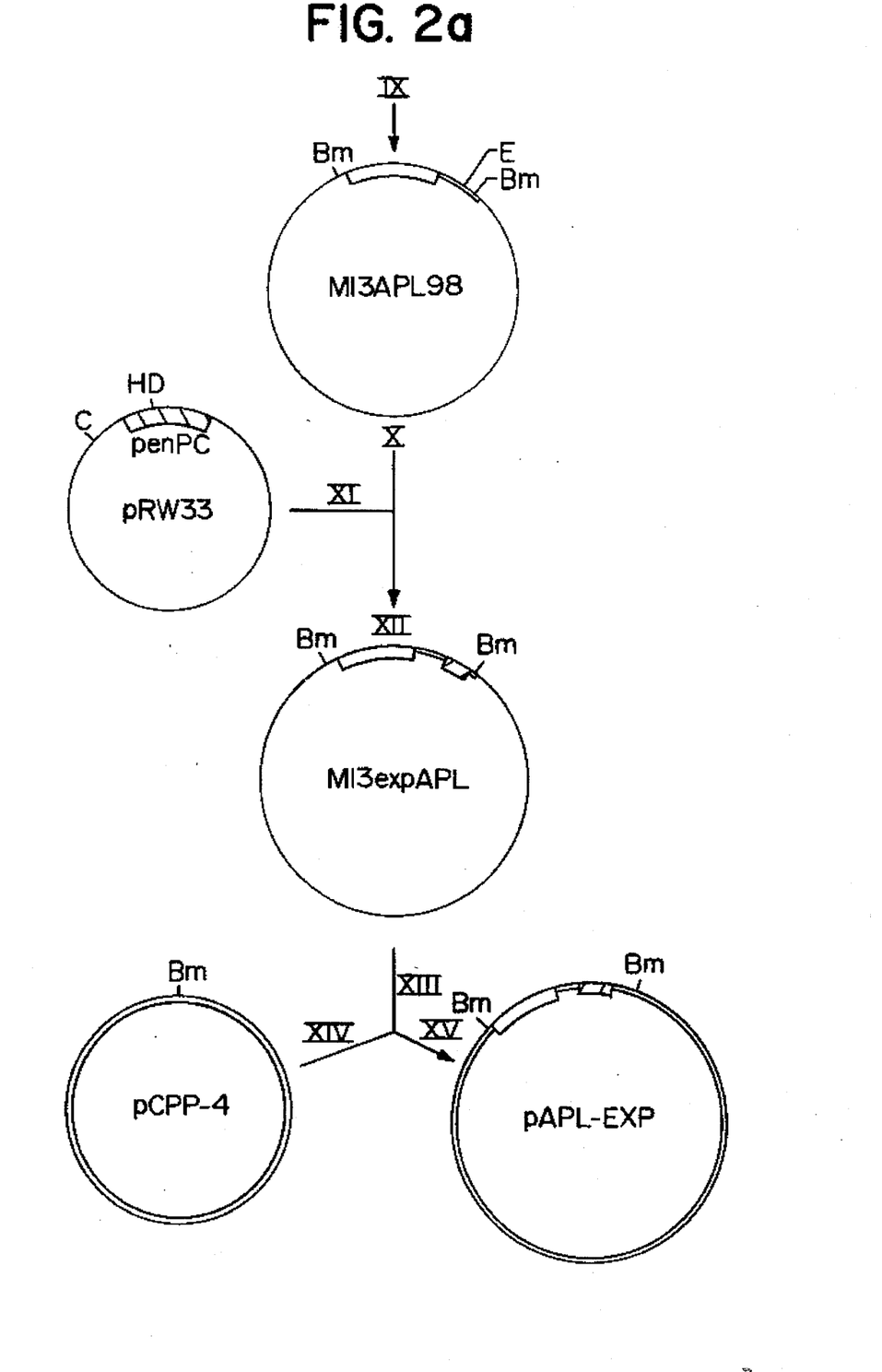

The oligonucleotide segments, JS96 and JS97 were dissolved to a concentration of 1 mg/mL in distilled water, and a 2 µg sample of each of these DNAs were then placed into 36 µL of water and incubated 20 minutes at 4° C. (Oligonucleotide segments used are shown in Table 3.) The DNA solution was then incubated with polynucleotide kinase as described in Molecular Cloning: A laboratory manual, T. Maniatis, E. F. Fritsch, J. Sambrook. The phosphorylated DNA was added to 1 µL of the digested M13 APL, and these DNAs were ligated with T4 DNA ligase as described in the reference above. This DNA was used to transform competent JM105, and the transformed cells were spread onto L-agar plates and incubated at 37° C. overnight. Twenty of the resulting phage plaques were propagated in 1.5 mL liquid cultures as described above, and the cells were used for small scale DNA isolation. Small volumes (3 µL of 50 µL) of these DNA preparations were then digested separately with BamHI and PvuII in 50 µL reactions and the resulting DNA fragments were analyzed by agarose gel electrophoresis as described above. Seven of the DNAs obtained were judged to contain the proper insert as they displayed the expected fragment pattern with these two endonucleases. Five of these preparations were then selected expression of the gene secreted into the medium in which the host is propagated to simplify its purification from other cellular products synthesized during cell growth. Therefore, it is advantageous to use DNA elements of the type defined above because they carry the proper secretion signals. The DNA sequences should be properly aligned so that the resulting chimeric gene encodes one reading frame that produces a hybrid product comprised of both proteins. This can be done, in the case of the penPC DNA sequence described above by digestion of plasmid pRW33 with endonucleases ClaI and HindIII and removal of the overhanging single stranded DNA segments by use of Mung-bean nuclease described by Maniatis et al. These DNA fragments could be separated by agarose gel electrophoresis, and the fragment of approximately 750 base pairs which contains the desired fragment could be isolated from the gel as described above. Phage DNA from M13APL98 can be digested with endonucleases EcoRV and the resulting DNA can be extracted with phenol:chloroform as described above. The isolated DNA fragment from pRW33 and the digested M13APL98 are then ligated as described above and the DNA is used to transform competent JM105. Several of the resulting plaques are then propagated in liquid culture and the cells which result from these incubations are used for small scale DNA preparations. Aliquots from these preparations are analyzed using agarose gel electrophoresis and those showing an increased size compared to M13APL98 are studied further. These isolates are then sequenced in the region comprising the penPC-APL fusion site using internal DNA primers and Sanger dideoxy nucleotide sequencing method as described for confirmation of the original APL clone. Those isolates which have the desired DNA sequence are then propagated in 25 mL cultures and DNA is isolated from them as described above. This new construct could then be named M13expAPL. The DNA could be digested with endonuclease BamHI in order to separate the chimeric gene from the phage DNA. The desired DNA could be isolated by agarose gel electrophoresis as described above, and could be placed into a vector that can replicate in *B. subtilis* and *E. coli* as described below. A diagram of the protocol is shown in FIGS. 2 and 2a.

Plasmid pCPP-4 (Band, L., Yansura, D. G. and Henner, D. J., Gene, Vol. 26, pp. 313–315, 1983, available as American Type Culture Collection acquisition No. 37277) could be digested with endonuclease BGmHI, extracted with phenol:chloroform and precipitated with ethanol as described above. This DNA is ligated to the DNA fragment carrying the chimeric gene described above and the resulting DNA is used to transform competent *E. coli*. The transformation mixture is then plated on L-agar media containing neomycin, the resistant transformants that arise are propagated, and DNA is prepared from these isolates by protocols commonly employed by those skilled in the art. These DNAs are analyzed by endonuclease digestion and agarose gel electrophoresis, and those which are composed of the DNA fragment encoding the chimeric gene fused to pCPP-4 are identified on the basis of their restriction fragment pattern as would be apparent to those skilled in the art. Since there is no direct method for selection of the desired plasmid, it is important to analyze several of the transformants at this point. Transformants whose plasmid DNA displays the desired pattern are then retransformed into competent *E. coli* as described above, and the resulting transformants are used to prepare cesium chloride purified DNA. These constructs can be identified as pAPL-EXP.

For ease of purification of the mutant and wild type forms of APL, it is advantageous to express the genes encoding these protein forms in a *B. subtilis* host which does not produce a neutral or alkaline proteases usually made by these bacteria (i.e. protease deficient). Therefore, it is best to transfer the pAPL-EXP into a host strain carrying the desired mutations such as GX4926 deposited at USDA Northern Regional Research Laboratory, Peoria, Ill., with accession Number B-15811 and described in WO 86/01825. However, protease-deficient *B. subtilis* strains are not capable of taking up DNA by the usual protocols and therefore a protoplast transformation protocol such as described in Mol. Gen. Genet., 168, pp 111–115, by Chang, S., and Cohen, S. N. will be required for transfer of the plasmid. The transformants are selected for neomycin resistance, and the plasmids present in them are isolated by the small scale DNA isolation protocol described earlier. Those transformants whose plasmids display a restriction pattern identical to pAPL-EXP are grown in liquid medium containing neomycin.

During growth of the transformants, the optical density of the culture and the alkaline protease activity of the medium are monitored. When significant levels of activity are seen, the cells are removed from the medium by centrifugation. The APL protease is then purified from the medium by standard biochemical techniques.

In order to express the modified forms of the APL gene altered in the region encoding amino acids 99 to 108 produced by site directed mutagenesis, it is necessary to insert the mutated DNA sequence into an expression vector. This can be done by digestion of the mutated M13 clones with endonucleases ScaI and SalI and gel isolation of the small fragment that would result from this digestion procedure. The clone M13expAPL is then also digested with these two endonucleases and the large DNA fragment is isolated as above. The two fragments are ligated together and used to transform competent JM105 cells. Several of the resulting plaques are propagated in liquid culture and this culture is then used to prepare template DNA for sequence confirmation of the clones. The mutant forms of the altered genes are transferred to the pCPP-4 vector and transformed into a protease deficient *B. subtilis* host as described above. The resulting transformants are propagated in liquid medium and the altered protein forms are purified as described above.

Demonstrations That The Mutant Protein Forms Have Increased Resistance to Autolytic Chain Cleavage The purified wild-type and mutant proteases are tested for their ability to resist autolysis. The proteins which are to be tested at a concentration ranging from 200 µg/mL to 10 mg/mL are first dialyzed against 200 mM sodium acetate buffer, pH 6.0. The solution is allowed to sit at room temperature for several days and the activity of the preparation is tested every three days for three weeks.

Those mutants having a larger fraction of the starting enzyme activity than that seen for the wild-type protein are more autolytically stable than the normal enzyme. Those proteins having the opposite character are less autolytically stable.

Example 2

SAVINASE

A major site of cleavage of the SAVINASE protease was identified by the method outlined in example 1 except that separation of the cleavage fragments was accomplished by use of a Sephadex G50 Superfine column. One of the pools isolated was subjected to automated protein sequence analysis and produced the sequence shown in Table 4. Since the entire amino acid sequence of SAVINASE is unknown, the sequence could not be directly compared to that of the intact protein. However, since alkaline proteases are very similar, a comparison of the derived sequence to other alkaline proteases could be performed to identify the region of the protein susceptible to autolytic cleavage. Computer assisted comparison of this sequence to that of APL indicated that this sequence is similar to this protein starting at amino acid 193 of the mature protein (see Table 5). The above sequence shows a high degree of similarity to this region of the protein and no other region displays a similarity greater than 33%, thus indicating that cleavage of the SAVINASE protease should take place in a region between amino acid 180–210, probably between amino acid 190–200 of the mature protein.

TABLE 4

AMINO TERMINAL SEQUENCE OF AN AUTOLYTIC FRAGMENT OF SAVINASE

| Cycle | 1 | 2 | 3 | 4 | 5 | 6 | 7 | 8 | 9 | 10 | 11 |
|---|---|---|---|---|---|---|---|---|---|---|---|
| Residues | NH₂—Gly | —Ala | —Gly | —Leu | —Asp | —Ile | —Val | —Ala | —Pro | —Gly | —Val— |

| Cycle cont. | 12 | 13 | 14 | 15 | 16 | 17 | 18 | 19 | 20 |
|---|---|---|---|---|---|---|---|---|---|
| Residues cont. | Asn | —Val | —Gln | —Ser | —Thr | —Tyr | —Pro | —Gly | —Ser— ... |

TABLE 5

COMPARISON OF THE SITES OF AUTOLYTIC DEGRADATION OF ESPERASE AND SAVINASE TO THE SEQUENCE OF APL IN THE REGION DISPLAYING HIGH SIMILARITY BETWEEN THE PROTEIN

| | |
|---|---|
| SAVINASE SEQUENCE | NH₂—Gly—Ala—Gly—Leu—Asp—Ile—Val—Ala—Pro—Gly—Val— |
| ESPERASE SEQUENCE | NH₂—Thr—Tyr—Gly—Pro—Glu—Ile—Glu—Ile—Ser—Ala—Pro—Gly—Val— |
| | NH₂—Gly—Pro—Glu—Ile—Glu—Ile—Ser—Ala—Pro—Gly—Val— |
| APL SEQUENCE | —Phe—Ser—Ser—Val—Gly—Ala—Glu—Leu—Glu—Val—Met—Ala—Pro—Gly—Ala— |
| | 190                                                                200 |
| SAVINASE cont. | Asn—Val—Gln—Ser—Thr—Tyr—Pro—Gly—Ser— ... |
| ESPERASE cont. | Asn—Val—Asn—Ser—Thr—Tyr—Thr—Gly—Asn— ... |
| | Asn—Val—Asn—Ser—Thr—Tyr—Thr—Gly—Asn— ... |
| APL cont. | Gly—Val—Tyr—Ser—Thr—Tyr—Pro—Thr—Asn— ... |
| | 210 |

Example 3

ESPERASE

A major site of cleavage in the ESPERASE protease was identified by the method in example 1 as modified in example 2. Automated sequence analysis of the peptides in one of the isolated pools generated the following double sequence shown in Table 6. Again the entire sequence of the protease is not known, and therefore a computer assisted sequence comparison was performed as for SAVINASE. These sequences are similar to other alkaline proteases at residues 193 and 191 of the mature proteins, and as expected, this sequence is also similar to the SAVINASE sequence listed above (see Table 5). The analysis indicates that the double sequence arose by cleavage of the protein between residues 180 to 210, probably between 185-200 of the mature protease and that two different cleavages occurred: one at a site two residues further in the sequence than the other. These data also indicate that cleavage of the protein can take place at the tyrosine residue present near the beginning of the double sequence. Since earlier results with APL indicated that tyrosine can be present at the site of autolytic cleavage, exposed tyrosine residues may be common to many cleavage sites in alkaline proteases.

Example 4

DETERGENT USE

An autolysis stable alkaline protease prepared by the method of this invention can be used as a detergent additive with the anionic/nonionic mixed detergents commonly available on the market. When added to a stock detergent base such as American Home Appliance Manufacturers Association (AHAM) standard phosphate-containing formulation, it will produce an enzyme/detergent mixture which can be used in washing. A detergent mixture containing a stable alkaline protease could be sold as a liquid formulation.

Many modifications and variations can be made to the practice of the present invention without departing from the spirit and scope thereof which is solely defined by the claims.

What is claimed is:

1. A method of increasing autolytic stability of an alkaline protease, comprising the steps of:
   a. identifying an autolytic cleavage site by:
      i. preparing an aqueous solution of an alkaline protease;

TABLE 6

AMINO TERMINAL SEQUENCE OF AN AUTOLYTIC FRAGMENT OF ESPERASE

| Cycle | 1 | 2 | 3 | 4 | 5 | 6 | 7 | 8 | 9 | 10 | 11 | 12 | 13 |
|---|---|---|---|---|---|---|---|---|---|---|---|---|---|
| Residues | NH₂—Thr | —Pro | —Glu | —Ile | —Glu | —Ile | —Glu | —Ile | —Pro | —Ala | —Val | —Asn | —Val— |
| | NH₂—Glu | —Tyr | —Gly | —Pro— | ... | — ... | —Ser | —Ala | —Ser | —Gly | —Pro | —Gly— | ... |

| Cycle cont. | 14 | 15 | 16 | 17 | 18 | 19 | 20 |
|---|---|---|---|---|---|---|---|
| Residues cont. | Asn—Ser | —Thr | —Ser | —Thr | —Gly | —Thr— | ... |
| | ... —Val | —Asn | —Tyr— | ... | —Tyr | —Asn— | ... | ii. rapidly inactivating the protease by the addition of trichloroacetic acid to prevent progressive degradation of peptide fragments produced by autolysis;
iii. separating the peptide fragments;
iv. resuspending the fragments in formic acid solution; and
v. identifying terminal amino acids of the separated fragments;

b. cloning a DNA fragment including a gene or segment thereof capable of encoding the portion of the protease containing the identified autolytic cleavage site; and c. mutating the cloned DNA fragment capable of encoding for the autolytic cleavage site, or amino acids in the vicinity of the autolytic cleavage site, by site directed mutagenesis;

whereby an alkaline protease having an increased autolytic stability relative to an non-modified alkaline protease is provided.

2. A method for increasing autolytic stability of an alkaline protease relative to a non-modified alkaline protease, comprising the steps of:

(i) identifying an autolytic cleavage site in the alkaline protease; and (ii) mutating a DNA fragment, which is capable of coding for the autolytic cleavage site or amino acids in the vicinity of the autolytic cleavage site, by site directed mutagenesis;

whereby the modified alkaline protease having increased autolytic stability relative to the non-modified alkaline protease is expressed thereby.

3. A modified alkaline protease having increased autolytic stability relative to a non-modified alkaline protease, said modified alkaline protease consisting essentially of a single mutation due to the modification of a DNA fragment capable of encoding said alkaline protease, said single mutation being located at or in the vicinity of an autolytic cleavage site in said alkaline protease.

4. The modified alkaline protease of claim 3, wherein the modified alkaline protease is produced by a microorganism.

5. A modified alkaline protease of *Bacillus licheniformis* having increased autolytic stability relative to a non-modified alkaline protease of *Bacillus licheniformis*, said modified alkaline protease being obtained by modifying said alkaline protease at or in the vicinity of autolytic cleavage sites that are located in said alkaline protease between amino acid residues numbered 102 to 105 and between amino acid residues numbered 163 and 164.

6. A modified alkaline protease having increased autolytic stability relative to a non-modified alkaline protease, said modified alkaline protease being obtained by modifying said alkaline protease which comprises the following N-terminal amino acid sequence: H$_2$N-Ala-Gln-Ser-Val-Pro-Trp-Gly-Ile-Ser-Arg-Val-Gln-Ala-Pro-Ala-Ala, at or in the vicinity of an autolytic cleavage site that is located in a region of said alkaline protease having an amino acid sequence that has greater than 33% homology to an amino acid sequence of an alkaline protease produced by *B. licheniformis*, at a region between amino acid residue numbers 180 and 210 of said alkaline protease produced by *B. licheniformis*.

7. A modified alkaline protease having increased autolytic stability relative to a non-modified alkaline protease, said modified alkaline protease being obtained by modifying said alkaline protease which comprises the following N-terminal amino acid sequence: H$_2$N-Gly-Thr-Val-Pro-TrP-Gly-Ile-Ser-Phe-Ile-Asn-Thr-Gln-Gln-Ala-His, at or in the vicinity of an autolytic cleavage site that is located in a region of said alkaline protease having an amino acid sequence that has greater than 33% homology to an amino acid sequence of an alkaline protease produced by *B. licheniformis*, at a region between amino acid residue numbers 180 and 210 of said alkaline protease produced by *B. licheniformis*.

* * * * *